(12) United States Patent
Schuijers et al.

(10) Patent No.: US 10,365,120 B2
(45) Date of Patent: Jul. 30, 2019

(54) DEVICE, METHOD AND SYSTEM FOR COUNTING THE NUMBER OF CYCLES OF A PERIODIC MOVEMENT OF A SUBJECT

(71) Applicant: KONINKLIJKE PHILIPS N.V., Eindhoven (NL)

(72) Inventors: Erik Gosuinus Petrus Schuijers, Eindhoven (NL); Louisa Simone Ruijs, Eindhoven (NL); Francesco Sartor, Eindhoven (NL); Paul Marcel Carl Lemmens, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 14/956,806

(22) Filed: Dec. 2, 2015

(65) Prior Publication Data

US 2016/0161281 A1 Jun. 9, 2016

(30) Foreign Application Priority Data

Dec. 3, 2014 (EP) ..................................... 14195989

(51) Int. Cl.
  *G01C 22/00* (2006.01)
  *G01P 13/00* (2006.01)
  (Continued)

(52) U.S. Cl.
  CPC .......... *G01C 22/006* (2013.01); *A61B 5/1118* (2013.01); *A61B 5/1123* (2013.01);
  (Continued)

(58) Field of Classification Search
  USPC ....................................................... 702/160
  See application file for complete search history.

(56) References Cited

U.S. PATENT DOCUMENTS 7,334,472 B2  2/2008 Seo
2003/0018430 A1  1/2003 Ladetto
(Continued)

FOREIGN PATENT DOCUMENTS

JP    2006293860 A    10/2006
JP    2006293861 A    10/2006

OTHER PUBLICATIONS

Wikipedia: Spectral Density [online], Aug. 2014 [retrieved on Nov. 20, 2018]. Retrieved from the Internet: <URL: https://web.archive.org/web/20140813214117/https://en.wikipedia.org/wiki/Spectral_density>. (Year: 2014).*

(Continued)

*Primary Examiner* — Paul D Lee

(57) ABSTRACT

The present invention relates to device, system and method for counting the number of cycles of a periodic movement of a subject, e.g. for step counting of a person. To enable more precisely counting the number of cycles of a periodic movement of a subject based on discontinuous accelerometer data the proposed device comprises an input unit (21) for receiving discontinuous accelerometer data over time indicating movement of at least a body part of the subject, a classifier (22) for classifying the movement of the subject into one of several movement classes based on said discontinuous accelerometer data, each movement class being related to a different range of speed of a periodic movement, a storage (23) for storing a table including for each movement class a periodicity value per time unit, and a movement calculation unit (24) for calculating the number of cycles of the periodic movement of the subject per time unit, for a predetermined time or continuously over time by use of the periodicity of the movement class, into which the movement has been classified.

20 Claims, 5 Drawing Sheets

(51) Int. Cl.
*G01P 15/18* (2013.01)
*A61B 5/00* (2006.01)
*A61B 5/11* (2006.01)

(52) U.S. Cl.
CPC ............ *A61B 5/7264* (2013.01); *G01P 13/00* (2013.01); *G01P 15/18* (2013.01); *A61B 5/681* (2013.01); *A61B 2560/0209* (2013.01); *A61B 2562/0219* (2013.01)

(56) References Cited

U.S. PATENT DOCUMENTS

| | | | | |
|---|---|---|---|---|
| 2004/0186695 | A1* | 9/2004 | Aoshima | G01C 22/006 |
| | | | | 702/190 |
| 2005/0205656 | A1 | 9/2005 | Sugai | |
| 2006/0123905 | A1 | 6/2006 | Bremer | |
| 2006/0174685 | A1 | 8/2006 | Skvortsov | |
| 2007/0054778 | A1* | 3/2007 | Blanarovich | A61B 5/103 |
| | | | | 482/8 |
| 2008/0243432 | A1 | 10/2008 | Kato | |
| 2009/0128342 | A1* | 5/2009 | Cohen | A61B 5/0205 |
| | | | | 340/573.1 |
| 2010/0100012 | A1* | 4/2010 | Matsumura | A61B 5/1118 |
| | | | | 600/595 |
| 2013/0072765 | A1* | 3/2013 | Kahn | A61B 5/01 |
| | | | | 600/301 |
| 2013/0132753 | A1* | 5/2013 | Priel | G06F 1/3203 |
| | | | | 713/323 |
| 2013/0190903 | A1 | 7/2013 | Balakrishnan | |
| 2013/0191034 | A1* | 7/2013 | Weast | G06F 17/00 |
| | | | | 702/19 |

OTHER PUBLICATIONS

Naqvi, Najme Z. et al "Step Counting Using Smartphone-Based Accelerometer", International Journal on Computer Science and Engineering, vol. 4, No. 5, May 2012, pp. 675-681.

Foerster F. et al "Detection of Posture and Motion by Accelerometry: a Validation Study in Ambulatory Monitoring", Abstract Only Sep. 1999, vol. 15, Issue 5.

Bao, Ling et al "Activity Recognition from User-Annotated Acceleration Data", Lecture Notes in Computer Science, vol. 3001, Abstract Only, 2004.

Poper, David M. et al "Development of Novel Techniques to Classify Physical Activity Mode using Accelerometers", Medicine & Science in Sports & Exercise, 2006.

* cited by examiner

US 10,365,120 B2

DEVICE, METHOD AND SYSTEM FOR COUNTING THE NUMBER OF CYCLES OF A PERIODIC MOVEMENT OF A SUBJECT

FIELD OF THE INVENTION

The present invention relates to a device, a corresponding method and a system for counting the number of cycles of a periodic movement of a subject, for instance for counting the number of steps of a person during running or walking.

BACKGROUND OF THE INVENTION

Currently there is an increased interest in devices that can unobtrusively monitor physiological/lifestyle parameters, e.g. estimate the energy expenditure using accelerometers. Today many of such devices are intended for fitness/sports monitoring (e.g. Nike Fuelband, MIO Alpha), but it is expected that such type of monitoring will become a commodity.

In order to make such devices attractive, they must be comfortable to wear, which means that they should be small and light. Therefore, battery size/power is an important design constraint. The less frequent the device needs to be recharged, the more user friendly it will be.

Different strategies are known to reduce battery power, e.g. one approach is to limit the sampling frequency of the physiological/lifestyle parameters, requiring less processing power on the subsequent algorithms. Another approach is to sample at a higher sampling frequency, but only for a limited amount of time. Such an approach is e.g. described in US 2006/123905 A1. This interrupted way of sampling has the advantage that, depending on the processor type, the corresponding processor sampling the signal can effectively be set to sleep, requiring only a very limited amount of battery power.

One of the interesting parameters to monitor using a lifestyle monitoring device is the number of steps taken during a certain time period, e.g. during the day, or, more generally, the number of cycles of a periodic movement, which may be steps, jumps, swimming strokes, revolutions during cycling, etc. With existing algorithms for continuous 3D accelerometer signals the 3D accelerometer signal is first processed to a 1D signal in which the periodicity of the accelerometer signal is clearly visible. On this pre-processed signal a fixed or variable threshold is set, that sets a flag at each time instance that the threshold is superseded. Finally, the number of threshold passings is simply counted.

For continuous sampling this is a suitable approach. However, for discontinuous sampling strategies this approach can lead to problems. Since only a limited amount of data is available, the periodicity of the signal is hardly visible anymore. Setting the (adaptive) threshold correctly becomes an issue, since the context is not visible anymore. In addition, some form of intra/extrapolation needs to occur in order to estimate the number of steps.

Hence, there is a need for an approach that is suitable for more precisely counting the number of cycles of a periodic movement of a subject if only discontinuous accelerometer data are available, e.g. to save battery power during the acquisition of the accelerometer data.

US2006/174685A1 discloses a method and apparatus for counting the steps taken by a walker, where the method includes detecting an acceleration value generated by a step taken by a walker at every first stated interval, calculating a standard deviation of detected acceleration values at every second stated interval, determining a walking mode corresponding to the calculated standard deviation among first through Nth walking modes as a walking pattern of the walker, in which N is a positive integer that is larger than 1, checking if there is at least one absolute value that is larger than a threshold acceleration value corresponding to the determined walking mode among the absolute values of the detected acceleration values, and incrementing a count value as a step taken by the walker if there is at least one absolute value that is larger than the threshold acceleration value among the absolute values of the detected acceleration values.

U.S. Pat. No. 7,334,472B2 discloses a method for measuring quantity of exercise and an apparatus comprising an acceleration sensor for generating acceleration information by measuring the quantity of exercise according to user movement, sensor control unit for supplying power to the acceleration sensor and sampling the acceleration information generated from the acceleration sensor, a dynamic energy measurement unit for converting the sampled acceleration information into dynamic energy, comparing a local maximum value with a predetermined threshold value if an ascending gradient of the dynamic energy has the local maximum value exceeding a predetermined value and determining a user step if the local maximum value exceeds the predetermined threshold value, a calorie consumption measurement unit for calculating calorie consumption by analyzing an energy level of dynamic energy determined as a user step, a memory for storing information, and a display section for displaying information related to the number of steps and calorie consumption.

SUMMARY OF THE INVENTION

It is an object of the present invention to provide device, method and system for more precisely counting the number of cycles of a periodic movement of a subject based on discontinuous accelerometer data indicating movement of at least a body part of the subject.

In a first aspect of the present invention a device for accurately counting the number of cycles of a periodic movement of a subject is presented comprising an input unit for receiving discontinuous accelerometer data over time indicating movement of at least a body part of the subject, a classifier for classifying the movement of the subject into one of several movement classes based on said discontinuous accelerometer data, each movement class being related to a different range of speed of a periodic movement, a storage for storing a table including for each movement class a periodicity value per time unit, and a movement calculation unit for calculating the number of cycles of the periodic movement of the subject per time unit, for a predetermined time or continuously over time by use of the periodicity of the movement class, into which the movement has been classified.

In a further aspect of the present invention a corresponding computer implemented method is presented.

In still another aspect of the present invention a corresponding system is presented comprising an accelerometer for acquiring discontinuous accelerometer data over time indicating movement of at least a body part of the subject, a device as disclosed herein for determining the number of cycles of the periodic movement based on the discontinuous accelerometer data acquired by the accelerometer, an output interface for outputting the determined number of cycles.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed system and as defined in the dependent claims.

The present invention is based on the idea to classify the activity (a periodic movement of the subject), i.e. to determine the kind of movement state and/or the movement class of the subject, e.g. a person doing sports or just moving as usual. For instance, three movement classes of a three-state classifier used for counting the number of steps of a person may be "walking", "not walking" and "running" distinguished by the different speed of the periodic movement "walking". However, the present invention may also be used to distinguish walking from cycling or, even further, to distinguish different movement classes of walking and cycling by a classifier, which e.g. classifies the movement of the subject into the movement classes "walking slowly", "walking fast", "cycling slow", "cycling fast" and "no movement". Depending on the detected activity, i.e. the determined class of movement, the periodicity of the signal is determined by use of a predetermined table, and based on the periodicity the number of cycles of the periodic movement is determined.

The accelerometer may be worn by the subject at different wearing positions, such as neck, pocket, thigh and wrist. Preferably, the whole system, including the not only the accelerometer but also the device and an output interface (e.g. a display) is worn by the subject during the activity. In other embodiments the accelerometer signals may be transmitted to the device in any suitable way, e.g. in a wired or wireless manner, which may be effected on the fly (i.e. in real time during the activity) or later (i.e. in non-real time after the activity). The device may e.g. be an application running on a smart device, such as a smartphone, tablet, smart watch, fitness device, lifestyle device or computer.

The calculation of the number of cycles may be made per time unit (e.g. per minute, per hour, per day, per week, etc.), for a predetermined time (e.g. for a predetermined time set by the user, such as for three hours or a predetermined day) or continuously over time.

In a preferred embodiment said movement calculation unit is configured to use the periodicity and integrate it over a time period to obtain the number of cycles during said time period. This provides a rather simple way to roughly estimate the number of cycles. Increasing the number of different classes (i.e. by further refining the class "walking" into "normal walking", "slow walking" and "fast walking") used in the classification and, hence, the number of different values of periodicities assigned to the respective classes increases the accuracy of the calculation of the number of cycles.

In another embodiment said storage is configured to store two or more tables for different anthropometric data, in particular for different lengths, weights, body mass index, gender and/or age, each table including periodicity values adapted for respective anthropometric data, wherein said movement calculation unit is configured to select the table for obtaining the periodicity based on the anthropometric data of the subject. For instance, in step counting the height of the person has a strong influence since a taller person usually makes larger steps than a smaller person. Hence, for use in step counting there may be different tables for different heights of persons with different periodicities for each class of movement. Further, for instance for male, female and children there may be different tables. Generally, by use of such anthropometric data a strong increase of the accuracy of the calculation of the number of cycles can be obtained.

Preferably, said input unit is configured to receive anthropometric data of the subject. Such anthropometric data may e.g. be entered via a keypad or display, or they may be transmitted from another device of the system that stores such data, e.g. in a health record or other personal record. Preferably, the device is thus personalized before use.

In another embodiment said classifier is configured to determine one or more features indicative of the movement frequency from the accelerometer data and to use said one or more features for said classification. Different features can be used for this purpose, depending on the kind of activity and the efforts that shall be taken to obtain a desired accuracy of the calculation. In a preferred embodiment said classifier is configured to use as a feature the signal power of the high frequency components and/or of the low frequency components of the accelerometer data. Thus, a feature representative of the power of the high frequency components of the accelerometer signals reflecting the (high frequency) energy that propagates through the body into the device when, in step counting, a foot hits the ground can be used. Another useable feature is a feature representative of the total (low frequency) signal power.

In another embodiment the device further comprises a movement frequency estimation unit for estimating the movement frequency from said accelerometer data, wherein said movement calculation unit is configured to use said estimated movement frequency in the calculation of the number of cycles. The movement frequency estimation unit refines the frequency estimate provided by the classification. E.g. if the classifier indicates a class with a range from 1.5 to 2 cycles per second, the movement frequency estimation unit may be configured to estimate a frequency within this range. This refined frequency may then be used in further processing. This further improves the accuracy of the calculation of the number of cycles.

Preferably, the input unit is configured to obtain three-dimensional accelerometer data indicating in three different directions, in particular orthogonal directions. By use of 3D accelerometer data, as e.g. delivered from a conventional accelerometer, the class of movement can be determined more accurately.

Further, in an embodiment the input unit is configured to obtain samples of accelerometer data acquired at intervals, in particular at (e.g. regular) intervals in a range from 2 to 60 seconds and/or to obtain samples of accelerometer data, each sample segment having a time duration in the range from 0.5 to 5 seconds. An exemplary typical configuration may e.g. be that the accelerometer data itself is sampled for one second at 20 Hz, and then not sampled for the subsequent four seconds, sampled for one second at 20 Hz, etc. This non-continuous stream of samples is then analyzed, typically in fixed segments of 15 seconds, thus effectively containing three seconds of sampled data (and 12 "empty seconds").

In another embodiment the classifier is configured to subsequently evaluate subsequent segments of accelerometer data (e.g. segments of 60 seconds duration, including intervals of e.g. 1 second data and of e.g. 4 seconds no data), wherein the subsequent segments overlap in time (e.g. have an overlap of a predetermined duration, e.g. have an overlap of 55 seconds in the example of segments of 60 seconds duration). This improves the user experience. For instance, in the above example each 5 seconds a classification is done, and a count number is calculated, despite the fact that longer segments are used. Generally, there are different parameters which may be configured, e.g. by the user or the manufacturer, including the inherent sampling frequency of the accelerometer signal, the time interval in which data is sampled, the time interval in which no data is sampled, the segment length of the classifier, and the "hop size", i.e., the time after which an update of the estimate is provided.

The system preferably further comprises a data interface for obtaining anthropometric data, such as a keyboard, microphone, touchscreen, etc. or as a transmission/reception unit for contacting an external device to retrieve such data.

Further, the system preferably further comprises a housing for housing the accelerometer, the device and the output interface and a holding element for holding the housing at a body part of the subject. The system may e.g. be an integrated device, such as a body-worn wristband or wristwatch, or any other wearable device that can be worn e.g. at the wrist, arm, ankle, leg or even at the neck or head. In general, the present invention may be configured as or part of a wearable personal health monitoring device.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
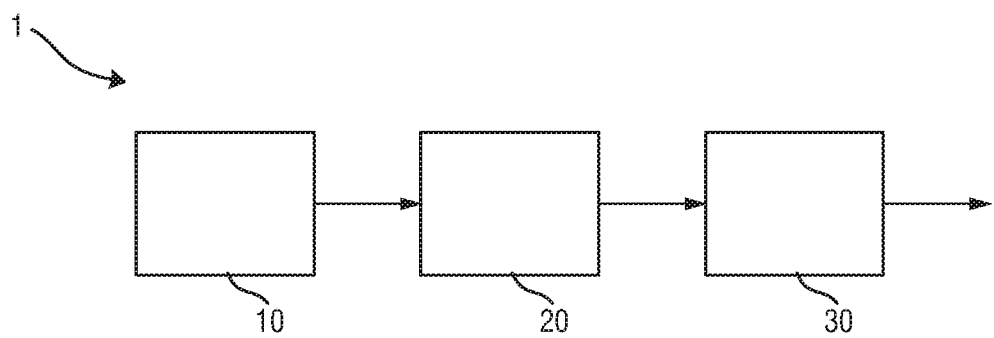
FIG. 1 shows a schematic diagram of an embodiment of a system according to the present invention.

FIG. 1 shows a schematic diagram of an embodiment of a system 1 for counting the number of cycles of a periodic movement according to the present invention. In the following the invention will be explained with reference to an exemplary embodiment in which it is used for counting the number of steps taken by a person, but the invention is also usable for counting the number of cycles of other periodic movements of a subject (e.g. a person or an animal), such as the number of rotations during cycling.

The system 1 comprises an accelerometer 10 for acquiring discontinuous accelerometer data over time indicating movement of at least a body part of the subject. Such accelerometers are generally known in the art. They can be worn e.g. around the leg or the arm, for instance a wrist worn device like a watch or at the ankle, but may also be mounted to any other part of the body. The accelerometer 10 generally provides three-dimensional accelerometer data, i.e. a separate accelerometer signal for each of three orthogonal directions indicating the acceleration in the respective direction. However, the invention also works with other accelerometer data, e.g. a single accelerometer signal (i.e. one-dimensional accelerometer data) or two-dimensional accelerometer data, as long as the desired periodic movement is in some way reflected in the accelerometer data.

The system 1 further comprises a device 20 for determining the number of cycles of the periodic movement based on the discontinuous accelerometer data acquired by the accelerometer 10. The device 20 may be implemented in hardware and/or software. E.g. a processor or computer may be configured accordingly to implement the elements of the device 20 as explained below.

The system 1 further comprises an output interface 30 for outputting the determined number of cycles. The output interface 30 may be a display for displaying the determined number, but may also be a transmitter for transmitting the determined number to another device, e.g. a smartphone, computer or website, for further processing (e.g. for medical purposes or storage in a health record) and/or display there.

All elements of the system 1 may be integrated into a common wearable device (as shown below in more detail for another embodiment of the system) or may be implemented as separate devices. For instance, only the accelerometer 10 is mounted to the subject's body and transmits the accelerometer data (in real time or non-real time; in a wired or wireless manner) to the device 20 for processing. The device 20 may be configured as or part of a computer, laptop, smartphone, tablet or any other device that is configured for carrying out the steps performed by the device 20.

Figure 2:
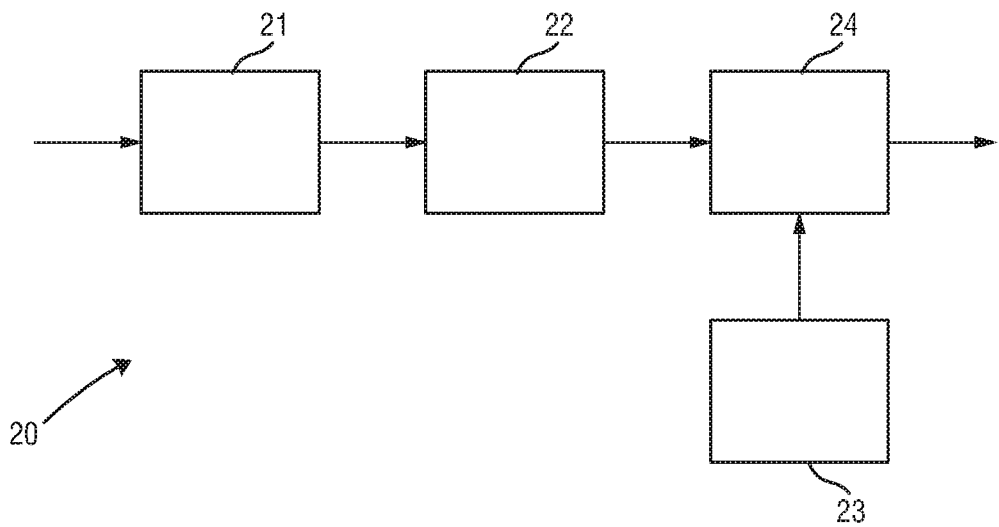
FIG. 2 shows a schematic diagram of an embodiment of a device according to the present invention.
Figure 3A:
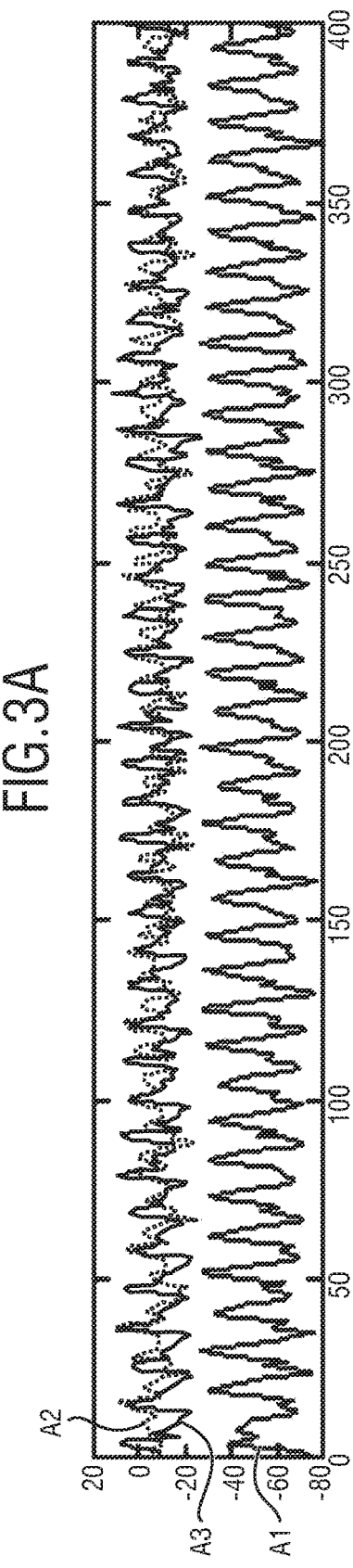
FIG. 3A and FIG. 3B show signal diagrams of continuous and discontinuous accelerometer signals.
Figure 3B:
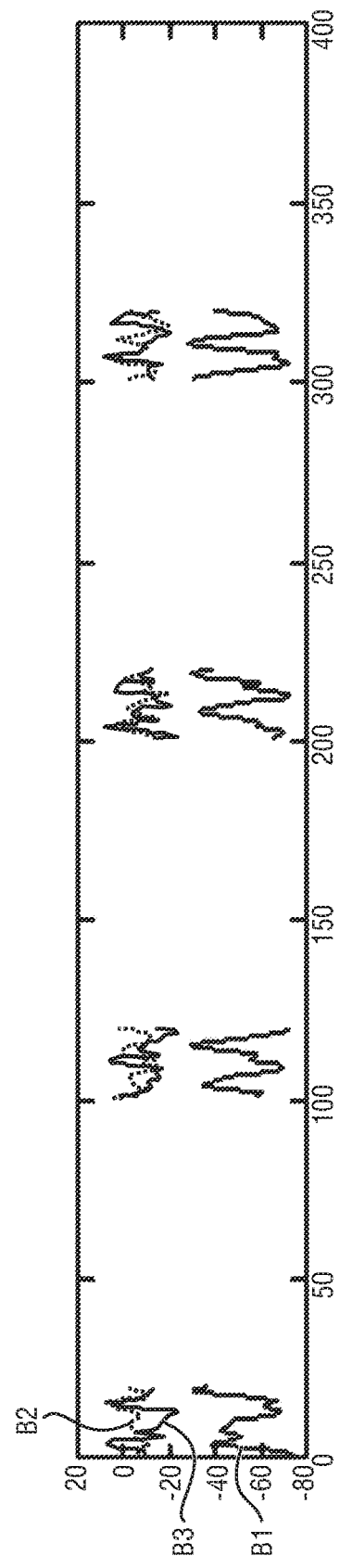

FIG. 2 shows a schematic diagram of an embodiment of a device 20 according to the present invention for counting the number of cycles of a periodic movement of a subject. The device 20 comprises an input unit 21 for receiving discontinuous accelerometer data over time indicating movement of at least a body part of the subject. Such discontinuous 3D accelerometer data are shown in FIG. 3B versus continuous 3D accelerometer data shown in FIG. 3A. In particular, FIG. 3A shows three continuous accelerometer signals A1, A2, A3 for three orthogonal directions and FIG. 3B shows three discontinuous accelerometer signals B1, B2, B3 for three orthogonal directions, which are actually samples of (in this example) a time duration of one second every five seconds, i.e. with an interruption of 4 seconds between the samples. During the interruptions the accelerometer 10 and/or the device 20 can thus be set to sleep mode to save battery power, which is an essential aspect in the use of such wearable devices. From the three accelerometer signals x, y, z the norm may e.g. be taken, e.g. the sqrt($x^2$+$y^2$+$z^2$), or the sum of abs(x)+abs(y)+abs(z) is formed.

The device further comprises a classifier 22 for classifying the movement of the subject into one of several movement classes based on said discontinuous accelerometer data, each movement class being related to a different range of speed of a periodic movement. There are several ways to perform this classification as will be explained below. In an exemplary simple embodiment used for step counting three different classes are distinguished including no walking, walking and running. In other more advanced embodiments many more classes are distinguished like no walking, slow walking, fast walking, running and sprinting.

A storage 23, such as a semiconductor memory element, stores a table including for each movement class a periodicity value per time unit. Thus, depending on the detected activity, the periodicity of the accelerometer signal(s) is estimated. In the simple example of using three classes, i.e. using a three-state classifier for distinguishing no walking, walking and running, the following pre-defined table may then be used to determine the periodicity:

| State | Periodicity (steps/second) |
| --- | --- |
| No walking | 0.0 |
| Walking | 1.9 |
| Running | 2.5 |

Finally, the number of cycles of the periodic movement of the subject is calculated by a movement calculation unit 24. This calculation is made per time unit (e.g. per hour, per day, etc.), for a predetermined time (e.g. 3 hours, 1 day, etc.) or continuously over time (e.g. updated every 15 seconds, every minute, etc.) by use of the periodicity of the movement class, into which the movement has been classified. Said periodicity is thus taken from the entry for said movement class in the table stored in the storage 23.

Thus, in a simple embodiment, if the classifier identifies the state of walking the periodicity of 1.9 is taken from the table. Based on an integration of this periodicity over time the number of steps is calculated resulting in 1.9×60=114 steps per minute or 6840 steps per hour.

The classification may be continuously or regularly done at predetermined intervals, e.g. once per minute or every 15 seconds so that the calculation of the number of steps can be updated accordingly. For instance, if the classifier 22 provides a state every 15 seconds, it would mean that the step count would increment to 28.5 after 15 seconds, 57 after 30 seconds, etc. Additional smoothing may be applied to provide the user with a better experience. For instance, instead of a stepwise increment every 15 seconds, the increment is conducted more often, but with smaller increments, e.g., after 7.5 seconds the step count would be incremented to 14 (0.25), after 15 seconds to 28.5, etc. In total, for instance, if the person walks for 15 minutes and then runs for 10 minutes the number of steps for this time period of 25 minutes would be 1.9×60×15+2.5×60×10=3210 steps.

As briefly mentioned above, one way to further improve the results is the use of a multi-level classifier that distinguishes more states and thus using a table having more entries. For instance, instead of just classifying no walking, walking and running more states could be applied, e.g.:

| State | Periodicity (steps/second) |
| --- | --- |
| No walking | 0.0 |
| Slow walking | 1.5 |
| Normal walking | 1.9 |
| Fast walking | 2.2 |
| Running | 2.5 |
| Sprinting | 2.7 |

In still other embodiments a multi-level classifier can even distinguish states of different kinds of movement, e.g. from cycling and walking. For instance, a classifier may classify the movement of the subject into the movement classes "walking slowly", "walking fast", "cycling slow", "cycling fast" and "no movement", i.e. having five classes and accordingly five periodicity values in a corresponding table.

Figure 4A:
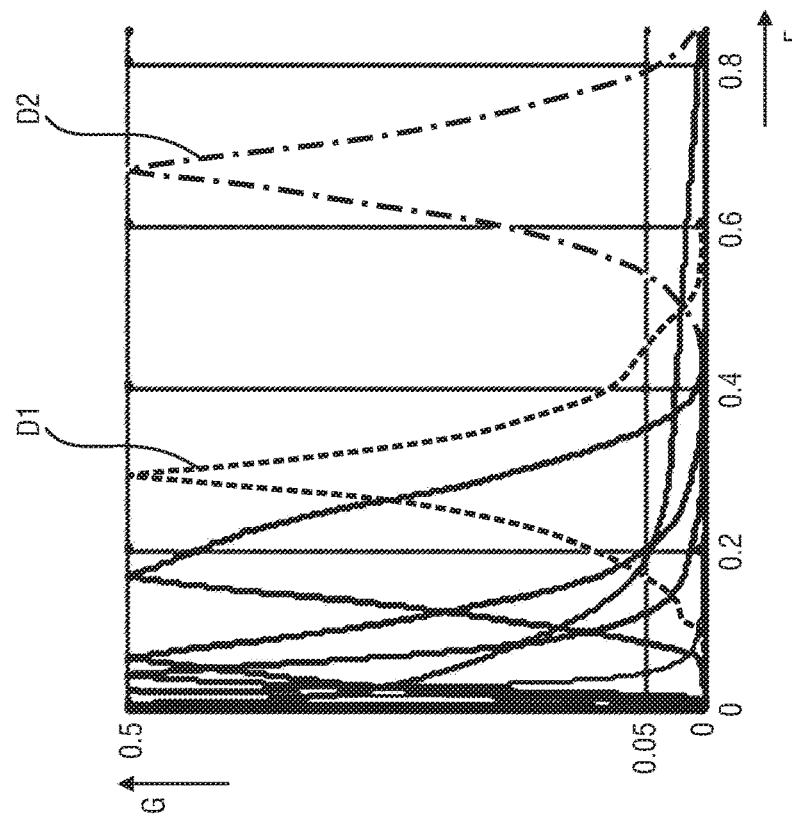
FIG. 4A and FIG. 4B show signal diagrams illustrating the use of different features derived from the accelerometer data.
Figure 4B:
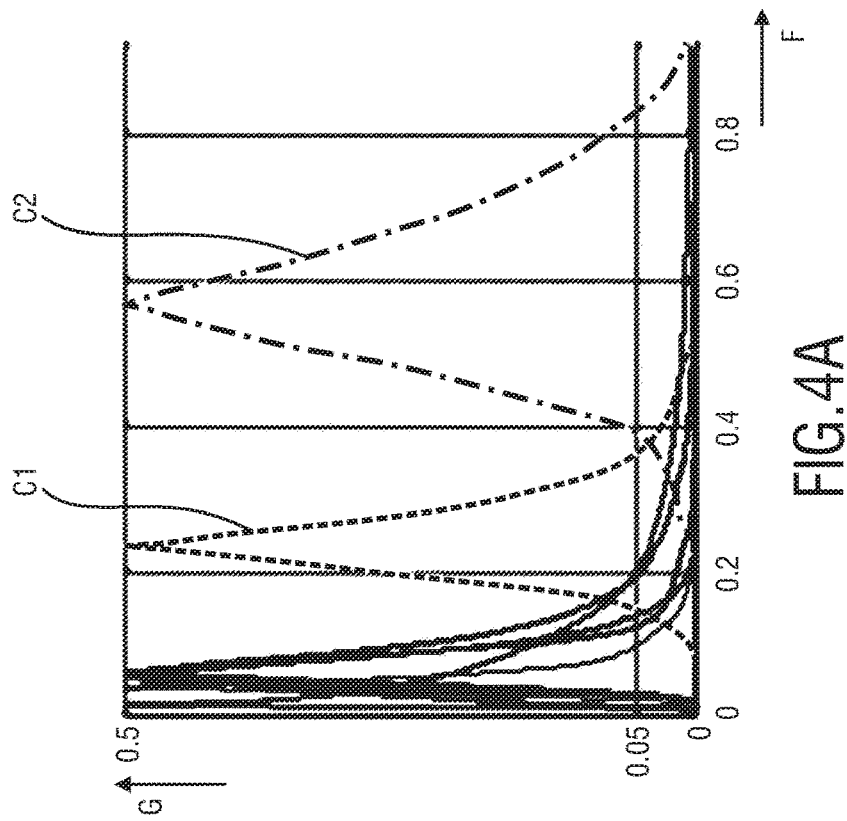

In the classification one or more features are used that are indicative for the respective movement states that shall be differentiated, e.g. that are indicative for distinguishing the state of walking from the states of running and no walking in the above mentioned simple embodiment. FIG. 4A and FIG. 4B show the folded cumulative distribution illustrating the use of two different features derived from the accelerometer data for different activities (i.e. movement states for the example of step counting). These features enable differentiation of the particular activities walking and running amongst themselves as well as from other activities. Hence these features represent a typical characteristic of the type of activity. FIG. 4A shows a folded cumulative distribution of a feature calculated as the power of the high frequency components of the accelerometer signals for different activities. The x-axis shows the feature value F and the y-axis shows the folded cumulative distribution G. A folded cumulative distribution is a cumulative distribution for which the upper half (the cumulative distributions higher than 0.5) is folded downwards. This helps to visually establish the median and dispersion of the cumulative distribution. The signal curve C1 is for the activity walking and the signal curve C2 is for the activity running. This feature substantially reflects the (high frequency) energy that propagates through the body into the device when a foot hits the ground. This feature may also be called the RMS amplitude of high frequency components of the accelerometer signals, which may be obtained by $$\sqrt{E((x-y_{lp})^2+(y-y_{lp})^2+(z-z_{lp})^2)}$$

wherein x, y, z represent the vectors of original sample values, $x_{lp}$, $y_{lp}$, $z_{lp}$ represent the vector of low-pass filtered samples and E( ) represents the expectation (mean) value.

FIG. 4B shows a folded cumulative distribution of the power of the low frequency components of the accelerometer signals for different activities. The signal curve D1 is for the activity walking and the signal curve D2 is for the activity running. This feature substantially reflects the total (low frequency) signal power. This feature may also be called the RMS vertical amplitude, which may be obtained by the variance of the signal g:

$$\sigma(g)$$

with $$g=\sqrt{((x_{lp})^2+(y_{lp})^2+(z_{lp})^2)},$$

wherein g is the norm of the total low frequency acceleration signal.

A classifier with more classes, e.g. a six state classifier as described above (no walking, slow walking, normal walking, fast walking, running and sprinting), could be developed based on the same two features. Since the distributions of the features for the different classes will be more overlapping than the case of three classes (no walking, walking and running) more classification errors may be made. However, since a misclassification into an adjacent class (e.g. classifying slow walking as normal walking) will only lead to a relatively small periodicity error, this can be tolerated.

Further features that may be useful in the classification can be found in L. Bao and S. Intille, "Activity recognition from user-annotated acceleration data," Pervasive Computing, vol. 3001, January 2004, pp. 1-17, Foerster F, Smeja M, Fahrenberg J., "Detection of posture and motion by accelerometry: a validation study in ambulatory monitoring," Computers in Human Behavior 1999; 15:571-583, and Pober D M, Staudenmayer J, Raphael C, Freedson P S, "Development of novel techniques to classify physical activity mode using accelerometers," Medicine and Science in Sports and Exercise 2006; 38:1626-1634.

Figure 5:
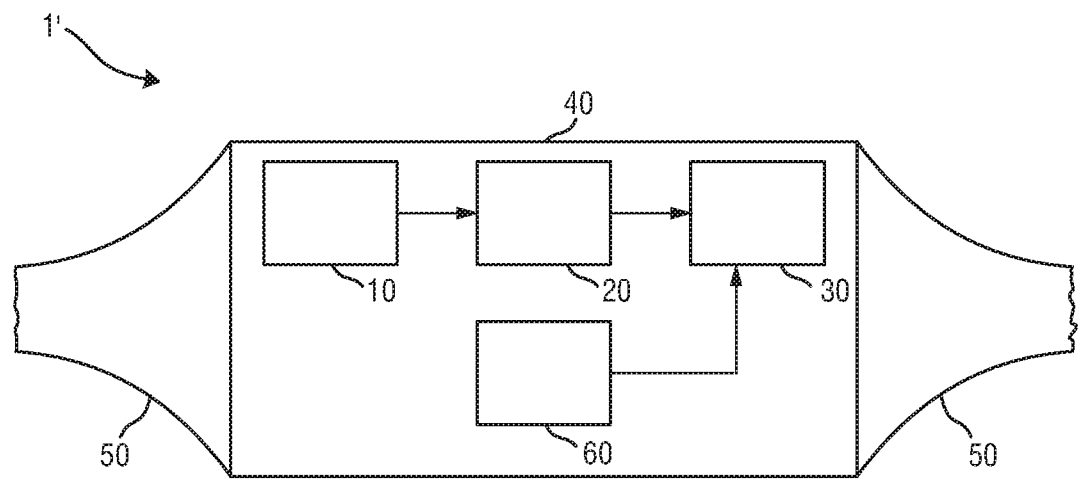
FIG. 5 shows a schematic diagram of another embodiment of a system according to the present invention.
Figure 6:
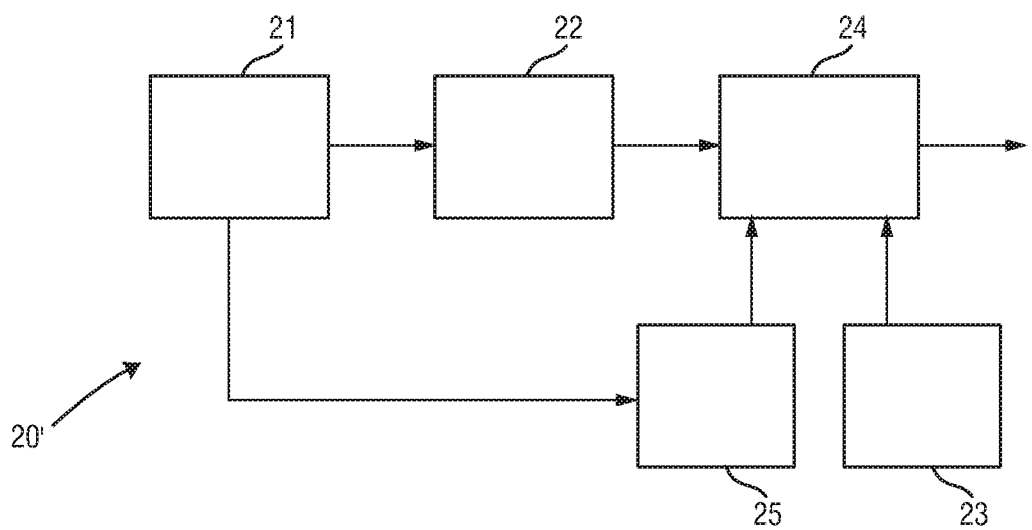
FIG. 6 shows a schematic diagram of an embodiment of a device according to the present invention.

FIG. 5 shows a schematic diagram of another embodiment of a system 1' and FIG. 6 shows another embodiment of a device 20' according to the present invention which may be used in the system 1 or 1'. In the system 1' a housing 40 is provided for housing the accelerometer 10, the device 20' and the output interface 30 to integrate all elements as an integrated wearable device. Further, a holding element 50, such as a belt or wrist band, is provided for holding the housing at a body part of the subject.

Preferably, the system 1' further comprises a data interface 60 for inputting anthropometric data, such as data about the length, weight, body mass index, gender, age or any other personal data of the person which may have an impact on the calculation of the number of cycles. For instance a taller person has a larger step size than a smaller person which should be taken into account to further increase the accuracy of the calculation. The data interface 60 may e.g. be a keyboard, touchscreen or other means for enabling a user to enter such data (e.g. on request by the system 1' when it is used for the first time). In another embodiment the data interface 60 may be a means for contacting an external device, such as a personal record or other data source, e.g. in the user's smartphone, storing such anthropometric data, so that the data interface 60 obtains such data automatically, e.g. when the system 1' is personalized for the user.

In the device 20' shown in FIG. 6 the input unit 21 is configured to receive anthropometric data of the subject, e.g. via the data interface 60 or directly as user input, e.g. via a keyboard or touchscreen.

Further, the storage 23 is configured to store two or more tables for different anthropometric data, in particular for different lengths, weights, body mass index, gender and/or age, each table including periodicity values adapted for respective anthropometric data. For instance, there may be separate tables for male and female users with different values of periodicity for the same class of activity (e.g. for "walking" the periodicity may be 1.9 for male users and 2.1 for female users), and/or there may be separate tables for persons with different sizes e.g. for sizes below 1.4 m, between 1.4 m and 1.6 m, between 1.6 m and 1.8 m, between 1.8 m and 2 m and above 2 m, etc. Thus, two or more criteria (i.e. kinds of anthropometric data) may be used for selecting the correct table for the actual user so that the appropriate values of periodicity are selected based on the classification, which further increases the accuracy of the calculated number of cycles.

As an alternative to storing and selecting a plurality of tables, the correct table for the user may be selected once and (solely) stored on in the storage, e.g. once the system is personalized. This information may, however, be updated if another user is going to use the system.

In another embodiment the device 20' (or also the system 1') further comprises a movement frequency estimation unit 25 for estimating the movement frequency from said accelerometer data. Further, the movement calculation unit 24 is configured to use said estimated movement frequency in the calculation of the number of cycles. On top of the movement state particular features may be used to adjust the periodicity estimate. One such feature may be an estimate of the actual frequency. Experiments have shown that this frequency in itself may not be a reliable parameter due to the discontinuity of the data. However, having both the knowledge of the classifier on the state, in combination with e.g. a frequency estimate, may improve the results over the periodicity obtained from the table. An alternative may be to use features that are correlated to the frequency. As can be seen from the folded cumulative distributions of FIG. 4, some features, that are not directly frequency estimates, are correlated to the speed and can be used to further improve the frequency estimate.

Figure 7:
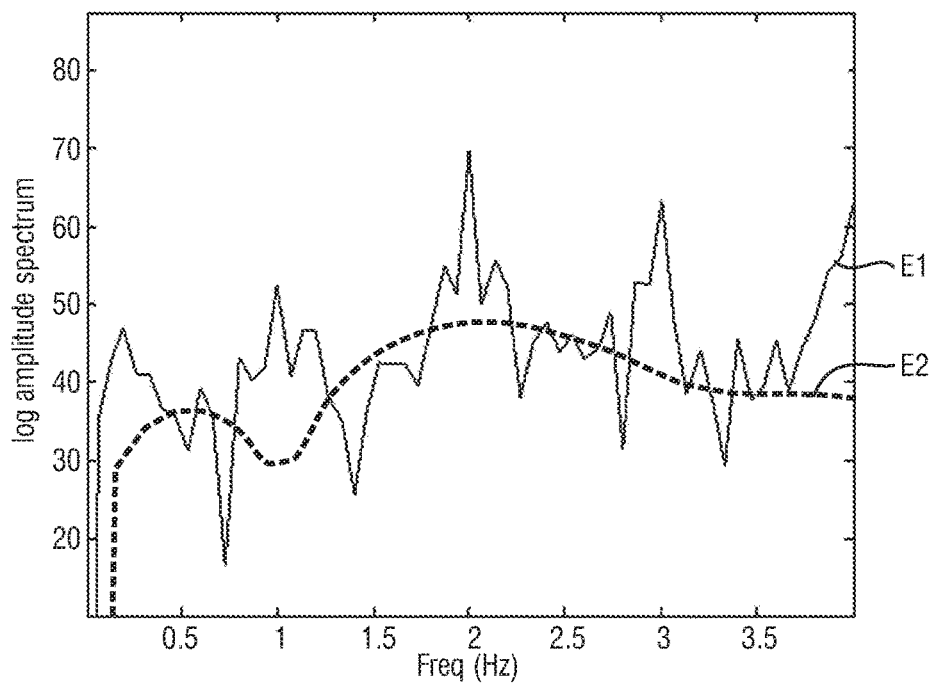
FIG. 7 shows a signal diagram illustrating an embodiment of the evaluation of the accelerometer data.

In an embodiment a typical window length for the classification may e.g. be 15 seconds. This means that only a total of three seconds are sampled of this 15 seconds window, namely second 1, second 6 and second 11, in the above mentioned example for the sampling of the accelerometer signal. The sampling frequency during these three seconds is 20 Hz resulting in 60 samples for an interval (window length used for the classification) of 15 seconds. To get a good frequency estimate based on this limited data in one embodiment an FFT of each 1 second window $x1[n]$, $x6[n]$ and $x11[n]$, all with $n=0, \ldots, 19$, is calculated leading to three spectral representations $X1[k]$, $X6[k]$ and $X11[k]$. The amplitude spectrum of these three spectral representations are then calculated and averaged. In FIG. 7, the corresponding spectra are shown for the continuous case (signal E1), where the stepping rate was obviously +/−2 Hz, and the non-continuous case (signal E2), where also the 2 Hz stepping rate can be estimated from.

Figure 8:
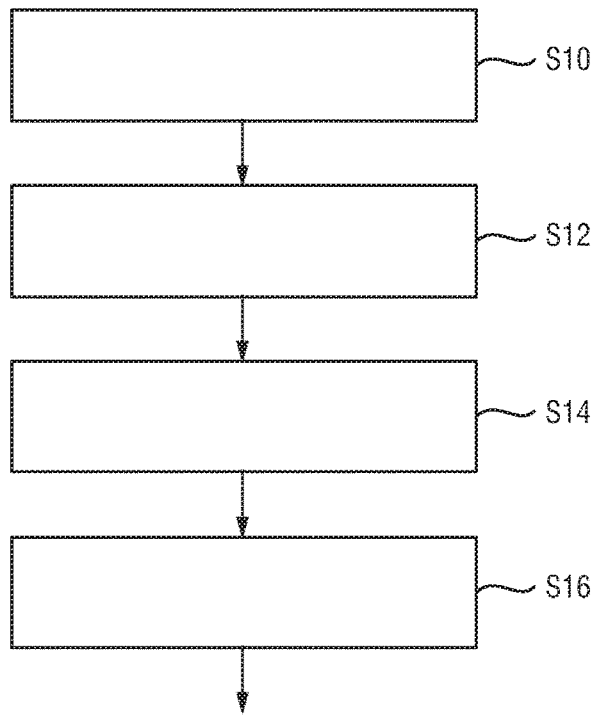
FIG. 8 shows a flow chart of an embodiment of a method according to the present invention.

FIG. 8 shows a flow chart of an embodiment of a method according to the present invention. In a first step S10 discontinuous accelerometer data over time indicating movement of at least a body part of the subject are received. In a second step S12 the movement of the subject is classified into one of several movement classes based on said discontinuous accelerometer data, each movement class being related to a different range of speed of the periodic movement. In a third step S14 a periodicity of the movement class, into which the movement has been classified, is retrieved from a table including for each movement class a periodicity value per time unit. In a fourth step S16 the number of cycles of the periodic movement of the subject is calculated per time unit, for a predetermined time or continuously over time by use of the retrieved periodicity. In the embodiment of the invention, the method is a computer implemented method.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A wearable device for counting the number of cycles of a periodic movement of a subject comprising:

an input unit for receiving discontinuous accelerometer data over time indicating movement of at least a body part of the subject;

a classifier for classifying the movement of the subject into one of several movement classes by analyzing a signal power of high or low frequency components of the accelerometer data of one or more features derived from said discontinuous accelerometer data, each movement class being related to a different range of speed of a periodic movement;

a storage for storing a table including for each movement class a periodicity value per time unit; and a movement calculation unit for calculating the number of cycles of the periodic movement of the subject per time unit, for a predetermined time or continuously over time by multiplying the periodicity value per unit time into which the movement has been classified by a time period during which the movement classification applies to the movement.

2. The wearable device as claimed in claim 1, wherein said movement calculation unit is configured to use the periodicity and integrate it over a time period to obtain the number of cycles during said time period.

3. The wearable device as claimed in claim 1, wherein said storage is configured to store two or more tables for different anthropometric data, in particular for different lengths, weights, body mass index, gender and/or age, each table including periodicity values adapted for respective anthropometric data, and wherein said movement calculation unit is configured to select the table for obtaining the periodicity based on the anthropometric data of the subject.

4. The wearable device as claimed in claim 3, wherein said input unit is configured to receive anthropometric data of the subject.

5. The wearable device as claimed in claim 1, wherein said classifier is configured to determine the one or more features indicative of a movement frequency from the accelerometer data and to use said one or more features for said classification.

6. The wearable device as claimed in claim 5, wherein said classifier is configured to use as a feature the signal power of the high frequency components and/or of the low frequency components of the accelerometer data.

7. The wearable device as claimed in claim 1, further comprising a movement frequency estimation unit for estimating a movement frequency from said accelerometer data, wherein said movement calculation unit is configured to use said estimated movement frequency in the calculation of the number of cycles.

8. The wearable device as claimed in claim 1, wherein the input unit is configured to obtain three-dimensional accelerometer data indicating in three different directions, in particular orthogonal directions.

9. The wearable device as claimed in claim 1, wherein the input unit is configured to obtain samples of accelerometer data acquired at intervals, in particular at intervals in a range from 2 to 60 seconds.

10. The wearable device as claimed in claim 1, wherein the input unit is configured to obtain samples of accelerometer data, each sample segment having a time duration in the range from 0.5 to 5 seconds.

11. The wearable device as claimed in claim 1, wherein during the receiving discontinuous accelerometer data over time, the wearable device enters a sleep mode periodically corresponding to when no data is received.

12. A computer implemented method implemented on a wearable device for counting the number of cycles of a periodic movement of a subject comprising:

receiving, from an accelerometer, discontinuous accelerometer data over time indicating movement of at least a body part of the subject;

classifying the movement of the subject into one of several movement classes by analyzing a signal power of high or low frequency components of the accelerometer data of one or more features derived from said discontinuous accelerometer data, each movement class being related to a different range of speed of a periodic movement;

retrieving a periodicity of the movement class, into which the movement has been classified, from a table including for each movement class a periodicity value per time unit; and calculating the number of cycles of the periodic movement of the subject per time unit, for a predetermined time or continuously over time by multiplying the periodicity value per unit time into which the movement has been classified by a time period during which the movement classification applies to the movement.

13. The method as claimed in claim 12, further comprising entering a sleep mode periodically corresponding to when no data is received during the receiving discontinuous accelerometer data over time.

14. The method as claimed in claim 12, wherein receiving comprises obtaining samples of accelerometer data acquired at intervals, in particular at intervals in a range from 2 to 60 seconds.

15. A system for counting the number of cycles of a periodic movement comprising:

an accelerometer for acquiring discontinuous accelerometer data over time indicating movement of at least a body part of the subject;

a device, comprising:

an input unit for receiving the discontinuous accelerometer data;

a classifier for classifying the movement of the subject into one of several movement classes by analyzing a signal power of high or low frequency components of the accelerometer data of one or more features derived from said discontinuous accelerometer data, each movement class being related to a different range of speed of a periodic movement;

a storage for storing a table including for each movement class a periodicity value per time unit; and a movement calculation unit for calculating the number of cycles of the periodic movement of the subject per time unit, for a predetermined time or continuously over time by multiplying the periodicity value per unit time into which the movement has been classified by a time period during which the movement classification applies to the movement; and an output interface for outputting the determined number of cycles.

16. The system as claimed in claim 15, further comprising a data interface for obtaining anthropometric data.

17. The system as claimed in claim 15, further comprising:

a housing for housing the accelerometer, the device and the output interface; and a holding element for holding the housing at a body part of the subject.

18. The system as claimed in claim 15, wherein during the receiving discontinuous accelerometer data over time, one or a combination of the device enters a sleep mode periodically corresponding to when no data is received or the accelerometer enters a sleep mode periodically.

19. The system as claimed in claim 15, wherein the input unit is configured to obtain samples of accelerometer data acquired at intervals, in particular at intervals in a range from 2 to 60 seconds.

20. The system as claimed in claim 15, wherein the input unit is configured to obtain samples of accelerometer data, each sample segment having a time duration in the range from 0.5 to 5 seconds.

* * * * *